United States Patent [19]

Ragusa et al.

[11] Patent Number: 5,972,716
[45] Date of Patent: Oct. 26, 1999

[54] FLUORESCENCE MONITORING DEVICE WITH TEXTURED OPTICAL TUBE AND METHOD FOR REDUCING BACKGROUND FLUORESCENCE

[75] Inventors: Robert P. Ragusa, Los Altos; Timothy M. Woudenberg, Moss Beach, both of Calif.; Jeffrey M. Marmaro, Aurora, Colo.

[73] Assignee: The Perkin-Elmer Corporation, Foster City, Calif.

[21] Appl. No.: 08/568,606

[22] Filed: Dec. 5, 1995

Related U.S. Application Data

[63] Continuation-in-part of application No. 08/235,411, Apr. 29, 1994, abandoned.

[51] Int. Cl.⁶ ........................................ C12Q 1/68
[52] U.S. Cl. ................. 436/172; 422/82.02; 436/63
[58] Field of Search ............... 422/82.08; 436/63, 436/172

[56] References Cited

U.S. PATENT DOCUMENTS

| | | | |
|---|---|---|---|
| 4,037,974 | 7/1977 | Fletcher et al. | 356/246 |
| 4,684,250 | 8/1987 | Kukka et al. | 356/246 |
| 4,737,764 | 4/1988 | Harrison | 340/114 R |
| 5,229,074 | 7/1993 | Heath et al. | 422/64 |
| 5,418,136 | 5/1995 | Miller et al. | 435/5 |
| 5,597,733 | 1/1997 | Bell et al. | 436/54 |

FOREIGN PATENT DOCUMENTS

| | | |
|---|---|---|
| 0 147 124 A2 | 7/1985 | European Pat. Off. . |
| WO 90/01168 | 2/1990 | WIPO . |
| WO 95/30139 | 11/1995 | WIPO . |

OTHER PUBLICATIONS

Higuchi et al., Bio/Technology 10, 413–417 (1992).
Higuchi et al., Bio/Technology 11, 1026–1030 (1993).

*Primary Examiner*—Kenneth R. Horlick
*Attorney, Agent, or Firm*—Carol A. Stratford; Vincent M Powers; Dehlinger & Associates

[57] ABSTRACT

An improved fluorescence monitoring apparatus for measuring fluorescent emission from a sample in response to sample irradiation by an emission beam is disclosed. The apparatus employs a sample tube having surface roughness characteristics which substantially reduce background fluorescence emission due to contamination of the tube holder in the apparatus. Also disclosed is a method of reducing such background, by texturing of a sample tube to produce desired roughness characteristics.

16 Claims, 9 Drawing Sheets

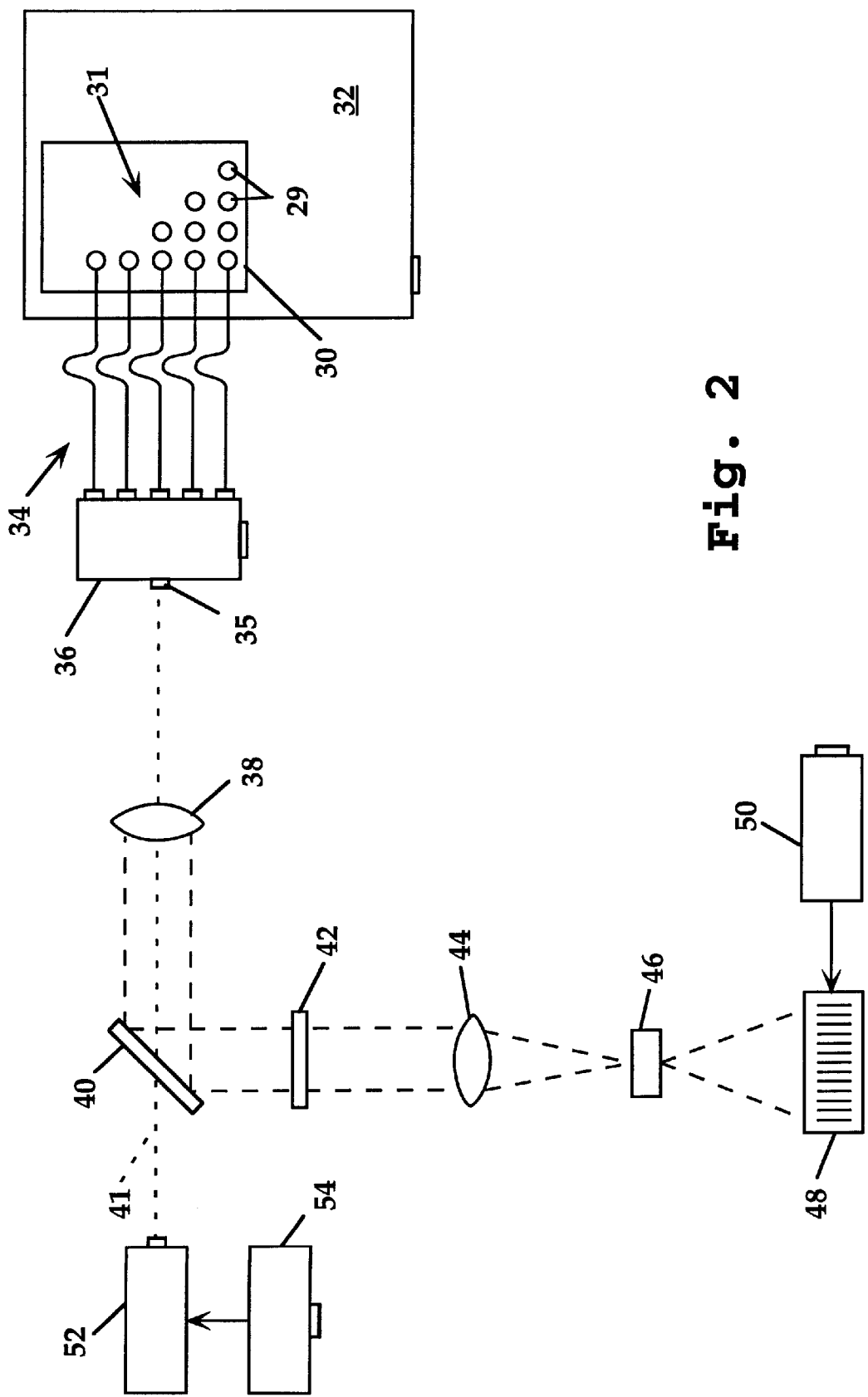

FLUORESCENCE MONITORING DEVICE WITH TEXTURED OPTICAL TUBE AND METHOD FOR REDUCING BACKGROUND FLUORESCENCE

This is a continuation-in-part of U.S. patent application Ser. No. 08/235,411 filed Apr. 29, 1994, abandoned.

FIELD OF THE INVENTION

The present invention relates to the field of reaction vessels adapted for use in fluorescent detection systems, and in particular, to a reaction vessel for use in a apparatus that employs fluorescence-based measurements of nucleic acid amplification products. The invention also includes a method for reducing fluorescent background in a fluorescence monitoring apparatus.

REFERENCES

Fung et al, U.S. Pat. No. 4,855,225
Menchen et al, U.S. Pat. No. 5,188,934
Bergot et al, International Patent Application PCT/US90/05565
Holland et al, Proc. Natl. Acad. Sci., 88: 7276–7280 (1991)
Karger et al, Nucleic Acids Research, 19: 4955 21962 (1991)
Keller and Manak, DNA Probes. Second Edition (Stockton Press, New York, 1993).
Lee et al, Nucleic Acid Research, 21: 3761–3766 (1993)
Walker et al., Nucleic Acids Research, 20:1691–1696 (1992). Hugland, pgs. 221–229 in Handbook of Fluorescent Probes and Research Chemicals, 5th Edition (Molecular Probes, Inc., Eugene, 1992)
Glazer et al, Proc. Natl. Acad. Sci., 87: 3851–3855 (1990)
Srinivasan et al, Applied and Theoretical Electrophoresis, 3: 235–239 (1993)
Kapuscinski et al, Anal. Biochem., 83: 252–257 (1977)
Hill, Anal. Biochem., 70: 635638 (1976) Setaro et al, Anal. Biochem., 71: 313–317 (1976)
Latt et al, J. Histochem. Cytochem., 24:24–33 (1976)
Rye et al, Nucleic Acids Research, 20: 2803–2812 (1992)

BACKGROUND OF THE INVENTION

Fluorescent detection of reaction products is common in a number of analytical settings. Typically, analytical instruments for monitoring fluorescent reactions are equipped with reaction chambers designed to minimize flourescence from external sources, for example, by providing a light-impermeable compartment constructed of non-fluorogenic materials. However, such precautions may not prevent fluorescent emissions from contamination sources, such as flecks of hair or skin introduced to the chamber during sample manipulation.

The present invention provides a sample tube which is constructed to reduce fluorescence from external sources. The tube is particularly usefull in nucleic acid amplification reactions, such as the polymerase chain reaction (PCR) in which progress of the reaction is monitored.

PCR has become a research tool of major importance with applications in cloning, analysis of genetic expression, DNA sequencing, genetic mapping, drug discovery, and the like, e.g. Arnheim et al (cited above); Gilliland et al, Proc. Natl. Acad. Sci., 87: 2725–2729 (1990); Bevan et al, PCR Methods and Applications, 1: 222–228 (1992); Green et al, PCR Methods and Applications, 1: 77–90 (1991); Blackwell et al, Science, 250: 1104–1110 (1990).

While a number of instruments have been developed for carrying out nucleic acid amplification, most employ basic PCR technology, e.g. Johnson et al, U.S. Pat. No. 5,038,852 (computer-controlled thermal cycler); Wittwer et al, Nucleic Acids Research, 17: 43534357 (1989)(capillary tube PCR); Hallsby, U.S. Pat. No. 5,187,084 (air-based temperature control); Garner et al, Biotechniques, 14: 112–115 (1993) (high-throughput PCR in 864-well plates); Wilding et al, International application No. PCT/US93/04039 (PCR in micro-machined structures); Schnipelsky et al, European patent application No. 90301061.9 (publ. No. 0381501 A2)(disposable, single use PCR device), and the like. Important design goals fundamental to PCR instrument development have included fine temperature control, minimization of sample-to-sample variability in multi-sample thermal cycling, automation of pre- and post-PCR processing steps, high speed cycling, minimization of sample volumes, real time measurement of amplification products, minimization of cross-contamination, or sample carryover, and the like.

Recently, PCR designs have focused on instruments that permit the amplification reaction to be carried out in closed reaction chambers and monitored in real time. Closed reaction chambers are desirable for preventing cross-contamination, e.g. Higuchi et al, Biotechnology, 10: 413417 (1992} and 11: 1026–1030 (1993) and Holland et al, Proc. Natl. Acad. Sci., 88: 72767280 (1991). Real time monitoring is particularly desirable in the analysis of diagnostic samples, where high frequencies of false positives and false negatives can severely reduce the value of the PCR-based procedure.

Moreover, real time monitoring of PCR permits far more accurate quantitation of starting target DNA concentrations in multiple-target amplifications, as the relative values of close concentrations can be resolved by taking into account the history of the relative concentration values during the PCR. Real time monitoring also permits the efficiency of the PCR to be evaluated, which can indicate whether PCR inhibitors are present in a sample.

Holland et al (cited above) and others have proposed fluorescence-based approaches to provide real time measurements of amplification products during PCR. Such approaches have either employed intercalating dyes (such as ethidium bromide) to indicate the amount of double stranded DNA present, or they have employed probes containing fluorescer-quencher pairs (the so-called "Tac-Man" approach) that are cleaved during amplification to release a fluorescent product whose concentration is proportional to the amount of double stranded DNA present.

Unfortunately, successful implementation of these approaches has been impeded because the required fluorescent measurements must be made against a very high fluorescent background. Thus, even minor sources of instrumental noise, such as the formation of condensation in the chamber during heating and cooling cycles, formation of bubbles in an optical path, particles or debris in solution, differences in sample volumes—and hence, differences in signal emission and absorbence, and the like, have hampered the reliable measurement of the fluorescent signals.

Parent U.S. patent application Ser. No. 08/235,411, abandoned, describes an apparatus that provides stable and reliable real time measurement of fluorescent indicators of amplification products resulting from any of the available nucleic acid amplification schemes. This apparatus operates by directing into a fluorescent mixture an excitation beam having appropriate energy to excite the fluorescent centers present in the mixture. The present invention is directed to an improvement of this apparatus which includes using a reaction tube that reduces background fluorescence measured from a test sample by reducing the amount of exogenous flourescence that enters the tube from outside sources such as contamination present in the apparatus tube-holder. As particularly described herein, the tube is a plastic consumable tube having an irregular or roughened outer surface that deflects or diffuses incident fluorescence emissions emanating from outside the tube. However, it is also preferable that the tube remain sufficiently clear to permit the human user to visualize fluid volume contained in the tube. Moreover, the tube may be sealable and provide a limited transparent window region to allow transmittance of an excitation beam to a sample held in the tube.

While the described tube is particularly suited for use in a PCR monitoring apparatus, such as that described in U.S. patent application Ser. No. 08/235,411, abandoned, it can be appreciated that such tubes are also suited for use in other instruments in which detection of light emissions is measured, and particularly those in which such measurement is carried out in a "plate-reader" format.

SUMMARY OF THE INVENTION

The invention includes, in one aspect, a fluorescence monitoring apparatus for measuring fluorescent emission from a sample in response to sample irradiation by an emission beam. The apparatus has an excitation beam source capable of directing an excitation beam into the sample, a tube-holder having a wall portion capable of supporting a tube, a tube for holding the sample, and a detector capable of detecting fluorescent emissions from the sample in the tube. The tube, which is typically formed of polycarbonate or polypropylene, is textured in the region of the tube supported by said tube-holder wall portion. The textured region is characterized by a surface roughness and peak density effective to significantly reduce background fluorescence detected by the detector in response to fluorescence emission related to contamination on the tube holder wall portion.

In a preferred embodiment, the tube has a textured outer surface characterized by a peak density of between about 50 and 500 peaks/0.5 inch line, more preferably 200 and 500 peaks/0.5 inch line. Also in a preferred embodiment, the surface roughness is characterized by an average depth of between 0.0002 and 0.003 inch, more preferably less than 0.001 inch.

In a related aspect the invention includes a method for reducing fluorescence background in a fluorescence monitoring apparatus designed for detecting fluorescent emission from a sample contained in a tube, where the tube is supported by wall portions of a tube-holder in the apparatus. The method includes texturing the surface region of the tube supported by the wall portion to produce a surface roughness effective to significantly reduce background fluorescence detected by the apparatus in response to fluorescence emission related to contamination on the tube holder wall portion.

In one general embodiment, the surface texturing is produced by casting the tube in a mold having an etched mold surface. In another embodiment, the outer surface region of the tube is abraded, e.g., by treatment with abrasive paper, to form the desired roughness characteristics, as above.

These and other objects and features of the invention will become more fully apparent when the following detailed description of the invention is read in conjunction with the accompanying drawings.

BRIEF DESCRIPTION OF THE FIGURES

FIG. 2 diagrammatically illustrates an apparatus of the invention configured for simultaneous monitoring of a plurality of amplification reactions by sequentially interrogating reactions via a fiber optic multiplexer;

DETAILED DESCRIPTION OF THE INVENTION

I. Definitions

Figure 1:
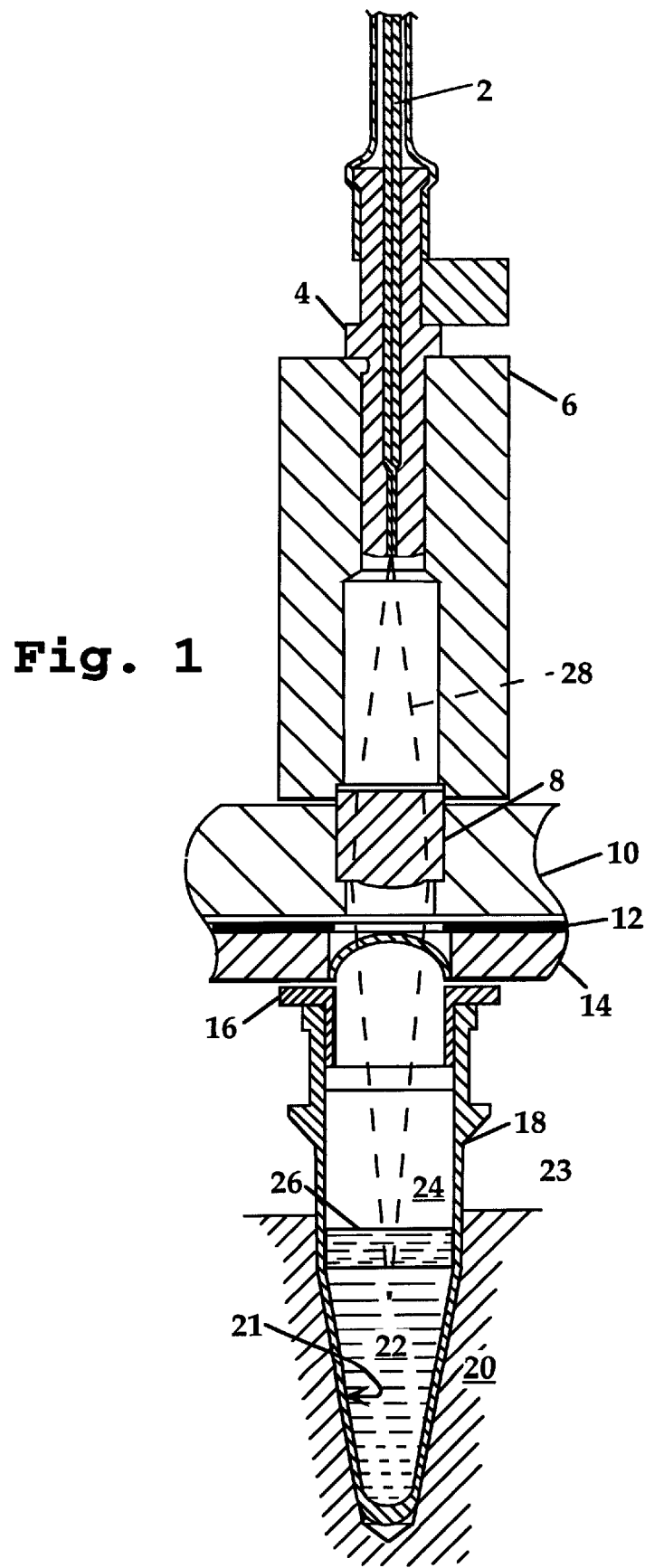
FIG. 1 diagrammatically illustrates the sample interface components of the apparatus of the invention, including the improved reaction vessel.

As used herein, the term "stable" in reference to a fluorescent signal means that the root means square (RMS) deviation in the signal due to noise is less than or equal to two percent of the average signal magnitude. More preferably, stable means that the RMS deviation in the signal due to noise is less than or equal to one percent of the average signal magnitude.

"Roughness" is a measure of peak-to-valley distances on a surface, and is commonly expressed as arithmetic average value of absolute distances above and below a reference plane along a line. A related measure of roughness is the average depth of the valleys forming the texture below a surface plane.

Another surface-texture property is "summit density" or "peak density", which provides a measure of peak density in a given surface area. Both roughness and peak density can be measured using a profilometer.

II. Real Time Detection Apparatus

A. Apparatus

The invention includes a fluorescence-based apparatus for monitoring in real time the progress of a nucleic acid amplification reaction, as described in U.S. patent application Ser. No. 08/235,411, abandoned, incorporated herein by reference. The type of amplification scheme used with the apparatus is not critical, but generally the apparatus requires either the use of a nucleic acid polymerase with exonuclease activity or a population of double stranded DNA which increases during the course of the reaction being monitored. Exemplary amplification schemes that may be employed with the apparatus of the invention include PCR, ligase-based amplification schemes, such as ligase chain reaction (LCR), Q-beta replicase-based amplification schemes, strand displacement amplification (SDA) schemes, such as described by Walker et al, and the like. A comprehensive description of nucleic acid amplification schemes is provided by Keller and Manak,—DNA Probes, Second Edition (Stockton Press, New York, 1993). Spectrally resolvable dyes suitable for use in the apparatus are disclosed in Fung et al, U.S. Pat. No. 4,855,225; Menchen et al, U.S. Pat. No. 5,188,934; Bergot et al, International Application PCTJUS90/05565; and like references.

The apparatus includes an excitation beam source capable of directing an excitation beam into a sample. Preferably this beam source is part of a sample interface—that is, optical components operationally associated with a closed reaction chamber which comprises a lens for focusing an excitation beam into the reaction mixture and for collecting the resulting fluorescence and a fiber optic for transmitting both the excitation beam from a light source to the lens and the fluorescent signals from the lens to a detection and analysis means. Preferably, the reaction mixture is contained in a closed reaction chamber, such as a closed tube, to prevent cross-sample contamination, or so-called "carryover." The lens focuses the excitation beam and collects fluorescence through a portion of a wall of the closed reaction chamber.

As mentioned above, the preferred reaction chamber is a tube, e.g. having the geometry of a conventional 200 μl "Eppendorf™" tube. The tube may closed after the reaction mixture is added by attaching a cap to the open end of the tube. In a preferred embodiment of the sample interface for PCR, the lens directs the excitation beam and collects fluorescence through a clear opening in the tube, illustrated as a clear cap in FIG. 1. According to an important aspect of the present invention, the reaction tube is manufactured to have optical characteristics which reduce background readings. This aspect of the invention is described in detail in Part B, below.

In the embodiment illustrated in FIG. 1, a first end fiber optic 2 is held by ferrule 4, housing 6, and plate 10 in a co-axial orientation with lens 8. A second end of fiber optic 2 (not shown) is operationally associated with a light source and detection and analysis means, discussed more fully below. The distance between the end face of fiber optic 2 and lens 8 is determined by several factors, including the numerical aperture of the fiber optic, the geometry of tube 18, the focal length of lens 8, the diameter of lens 8, and the like. Guidance for selecting values for such variables in any particular embodiment is readily found in standard texts on optical design, e.g. Optics Guide 5 (Melles Griot, Irvine, Calif., 1990), or a like reference. In the illustrated embodiment, lens 8 has a diameter of 8 mm and is composed of material BK7, available from Edmund Scientific (Barrington N.J.). Fiber optic 2 has a numerical aperture of 0.2. Preferably, the design permits maximal transmission of excitation beam 28 to reaction mixture 22. For example, lens 8, numerical aperture of fiber optic 2, and the distance between the end of fiber optic 2 and lens 8 are selected so that the diameter of lens 8 equals or exceeds the diameter of excitation beam 28 where beam 28 impinges on the lens (as illustrated in FIG. 1). Excitation beam 28 is focused through cap 16 of tube 18, void 24, and top surface 26 of reaction mixture 22 to a region approximately 1–3 times the diameter of the fiber optic just below, e.g. 1 –3 mm, surface 26. Tube 22 is positioned in tube-holder 23. This degree of focusing is not a critical feature of the embodiment; it is a consequence of adapting the sample interface to the geometry and dimensions of a sample holder of a commercially available thermal cycler. In other embodiments, the geometry and dimension may permit a sharper focus into the reaction mixture.

The lens of the apparatus may have a variety of shapes depending on particular embodiment and desired geometry of the sample to be tested. For example, the lens may be a sphere, truncated sphere, cylinder, truncated cylinder, oblate spheroid, or truncated oblate spheroid, or the like, and may be composed of any suitably transparent refractive material, such as disclosed by Hlousek U.S. Pat. No. 5,037,199; Hoppe et al, U.S. Pat. No. 4,747,87; Moring et al, U.S. Pat. No. 5,239,360; Hirschfield, U.S. Pat. No. 4,577,109; or like references.

With continued reference to FIG. 1, emitted fluorescent light given off by reaction mixture 22 in response to excitation beam 28 is collected by lens 8 along approximately the same optical pathway as that defined by excitation beam 28. The emitted light is focused onto the end of fiber optic 2 for transmission to optical separation and analysis components of the apparatus, discussed below. The beam source and focusing components just described are also referred to herein as an excitation beam source capable of directing an excitation beam into a sample.

In a preferred embodiment, the sample interface also includes means for heating the portion of the wall of the reaction chamber used for optical transmission, in order to reduce variability due to scatter and/or absorption of the excitation beam and signal from condensation of reaction mixture components. In the embodiment shown in FIG. 1, the portion of the reaction chamber (tube 18) wall used for optical transmission is tube cap 16. Accordingly, heating element 12 and heat-conductive platen 14 are employed to heat cap 16. Preferably, heating element 12 comprises resistance heating elements and temperature sensors that permit programmed controlled of the temperature of cap 16. Cap 16 is maintained at a temperature above the condensation points of the components of the reaction mixture. Generally, cap 16 may be maintained at a temperature in the range of 94–110° C. Preferably, cap 16 is maintained at a temperature in the range of about 102° C. to about 105° C., since the principal solvent in the reaction mixture is usually water. More preferably, cap 16 is maintained at 103° C. Preferably, in embodiments employing thermal cycling, the cap heating components described above are thermally isolated from heating conducting block 20 employed to cyclically control the temperature of reaction mixture 22. Block 20 defines one or more tube holders, each having a wall portion, such as holder 21 having wall portion 23, capable of supporting a tube, such as tube 18. As will be described below, the wall portion of the tube holder may have surface contaminants which can cause spurious fluorescence emission in the apparatus.

Selection of appropriate materials for the components described above is well within the skill of an ordinary mechanical engineer. Exemplary criteria for material selection include (i) degree of thermal expansion, especially for amplification schemes employing thermal cycling, and its effect on the alignment of the optical components, (ii) optical transmission properties in the excitation wavelengths and fluorophore emission wavelengths employed, (iii) chemical inertness of the reaction chamber relative to components of the reaction mixture, (iv) degree to which critical reaction components, e.g. polymerases, target nucleic acids, would tend to adsorb onto chamber walls, (v) minimization of fluorescent materials in the optical pathway, and the like. Typically, tubes containing amplification reaction mixtures are made of polypropylene, polycarbonate or like materials.

The sample interface shown in FIG. 1 may be employed individually or it may be employed as one of a plurality of identical interfaces in a single instrument, as shown diagrammatically in FIG. 2. In the illustrated embodiment, individual sample interfaces 31, arrayed in tube-holder 29 in block 30 (which may, for example, be a heating block associated with thermal cycler 32, such as described in Mossa et al, European patent application No. 91311090.4, publ. No. 0488769 A2) are connected by fiber optics 34 to fiber optic multiplexer 36, which selectively permits transmission between individual fiber optics and port 35, e.g under user control via a programmed microprocessor.

In a preferred configuration, excitation beam 41, generated by light source 52 and controller 54, passes through beam splitter 40 and is focused onto port 35 by lens 38, where it is sequentially directed by fiber optic multiplexer 36 to each of a predetermined set, or subset, of fiber optics 34. Conversely, with reference to the sample interface shown in FIG. 1, fluorescent signals generated in the reaction chambers are collected by lens 8 and focused onto a fiber optic which, in turn, transmits the signal to a detection and analysis means, possibly via a fiber optic multiplexer. Returning to FIG. 2, a fluorescent signal collected by a sample interface is directed to fiber optic multiplexer 36 where it emerges through port 35 and is collected and collimated by lens 38. Lens 38 directs the fluorescent signal to beam splitter 40 which, in turn, selectively directs the signal through cut-off filter 42, which prevents light from the excitation beam from reaching the signal detection components. Beam splitter 40 may be a conventional dichroic mirror, a fully reflective mirror with an aperture to pass the excitation beam (e.g. as disclosed in U.S. Pat. No. 4,577,109), or like component. After passing through cut-off filter 42, the fluorescent signal is directed by lens 44 to a spectral analyzer which spectrally separates the fluorescent signal and measures the intensities of a plurality of the spectral components of the signal. Typically, a spectral analyzer comprises means for separating the fluorescent signal into its spectral components, such as a prism, diffraction grating, or the like, and an array of photodetectors, such as a diode array, a charge-coupled device (CCD) apparatus, an array of bandpass filters and photomultiplier tubes, or the like. In the preferred embodiment shown in FIG. 2, the spectral analyzer comprises diffraction grating 46 (e.g., model CP-140, Jobin-Yvon, N.J.) and CCD array 48 (e.g., model S2135 Princeton Instruments, N.J.), which is linked to CCD controller 50.

An exemplary CCD array suitable for analyzing fluorescent signal from fluorescein and tetramethylrhodamine is partitioned into 21 collection bins which span the 500 nm to 650 nm region of the spectrum. Each bin collects light over an 8.5 non window. Persons skilled in the art will recognize that many alternative configurations may also be employed to achieve substantially the same end result. An exemplary application of a CCD array for spectral analysis is described by Karger et al, Nucleic Acids Research, 19: 4955 (1991). The components described above for detecting fluorescence emission from the samples in the tubes are also referred to herein, collectively, as detection means.

Analyzing the fluorescent signal based on data collected by a spectral analyzer is desirable since components of the signal due to one or more first fluorescent indicators and a second fluorescent indicator can be analyzed simultaneously to calculating intensity ratios without introducing wavelength-specific apparatus variability that might arise, e.g. by misalignment, in a apparatus based on multiple beam splitters, filters, and photomultiplier tubes. Also, a spectral analyzer permits the use of "virtual filters" or the programmed manipulation of data generated from the array of photo-detectors, wherein a plurality of discrete wavelength ranges are sampled —in analogy with physical bandpass filters— under programmable control via an associated microprocessor. This capability permits a high degree of flexibility in the selection of dyes as first and second fluorescent indicators.

Generally, the detection and analysis means may be any detection apparatus that provides a readout that reflects the ratio of intensities of the signals generated by the first and second fluorescent indicators. Such apparatuses are well know in the art, as exemplified by U.S. Pat. Nos. 4,577,109 and 4,786,886 and references such as The Photonics Design & Applications Handbook, 39th Edition (Laurin Publishing Co., Pittsfield, Mass., 1993).

Preferably, the apparatus of the invention is employed to monitor PCRS, although it may also be employed with a variety of other amplification schemes, such as LCR Descriptions of and guidance for conducting PCRs is provided in an extensive literature on the subject, e.g. including Innis et al (cited above) and McPherson et al (cited above). Briefly, in a PCR, two oligonucleotides are used as primers for a series of synthetic reactions that are catalyzed by a DNA polymerase. These oligonucleotides typically have different sequences and are complementary to sequences that (i) lie on opposite strands of the template, or target, DNA and (ii) flank the segment of DNA that is to be amplified. The target DNA is first denatured by heating in the presence of a large molar excess of each of the two oligonucleotides and the four deoxynucleoside triphosphates (dNTPs). The reaction mixture is then cooled to a temperature that allows the oligonucleotide primers to anneal to their target sequences, after which the annealed primers are extended with DNA polymerase. The cycle of denaturation, annealing, and extension is then repeated many times, typically 25–35 times. Because the products of one round of amplification serve as target nucleic acids for the next, each successive cycle essentially doubles the amount of target DNA, or amplification product.

As mentioned above an important aspect of the invention is the fluorescent dyes used as the first and second fluorescent indicators. By examining the ratio of the fluorescent intensities of the indicators, the effects of most sources of systematic variability, which would be apparent in the intensities alone, are eliminated. Generally, in accordance with the invention, the first fluorescent indicator may be a complex forming dye or a dye covalently attached to an oligonucleotide probe which is degraded during polymerization steps to generate a signal. This later embodiment relates to the so-called "Tacman" approach, described by Holland et al.) Proc. Natl. Acad. Sci., 88: 7276–7280 (1991). As used herein, the term "complex-forming" in reference to a dye means that the dye is capable of forming a stable non-covalent complex with either double stranded or triple stranded nucleic acid structures, usually DNA, and that the dye's fluorescent characteristics are substantially different in the complexed state as compared to a non-complexed, i.e. usually free-solution, state. Preferably, the quantum efficiency of fluorescence of a complex-forming dye is enhanced in the complexed state as compared to the free-solution state, thereby resulting in enhanced fluorescent upon complex formation. Exemplary complex-forming dyes include ethidium bromide, propidium iodide, thiazole orange, acridine orange, daunomycin, mepacrine, 4',640 diaminidino-2-phenylindole (DAPI), oxazole orange, bis-benzimidaxole dyes, such as Hoechst 33258 and Hoechst 33342, and heterodimers of various intercalating dyes, such as ethidium, acridine, thiazolium, and oxazolium dyes (known by their acronyms POPRO, BOPRO, YOPRO, and TOPRO), and like dyes, which are described in the following references: Haugland, pgs. 221–229 in Handbook of Fluorescent Probes and Research Chemicals, 5th Edition (Molecular Probes, Inc., Eugene, 1992); Glazer et al, Proc. Natl. Acad. Sci., 87: 3851–3855 (1990); Srinivasan et al, Applied and Theoretical Electrophoresis, 3: 235–239 (1993); Kapuscinski et al, Anal. Biochem., 83: 252–257 (1977); Hill, Anal. Biochem., 70: 635638 (1976); Setaro et al, Anal. Biochem., 71: 313–317 (1976); Latt et al, J. Histochem. Cytochem., 24:24–33 (1976); and Rye et al, Nucleic Acids Research, 20: 2803–2812 (1992). Preferably, when complex-forming dyes are employed as first fluorescent indicators, such dyes are selected from the group consisting of thiazole orange, ethidium bromide, and TOPRO.

Dyes employed as second fluorescent indicators include fluorescent dyes whose fluorescent characteristics are substantially unaffected by the presence or association with nucleic acids, particularly double stranded DNA. Such dyes may include virtually any fluorescent dye fulfilling this criterion which is also spectrally resolvable from the first fluorescent indicator employed in the particular reaction. Preferred second fluorescent indicators include rhodamine dyes and fluorescein dyes. More preferably, the second fluorescent indicator is tetramethylrhodamine or 2',4',5',7', tetrachloro-4,7-dichlorofluorescein, the latter being disclosed by Menchen et al, U.S. Pat. No. 5,188,934.

In a preferred embodiment, a first fluorescent indicator and a second fluorescent indicator are both covalently attached to an oligonucleotide probe as described by Lee et al, Nucleic Acid Research, 21: 3761–3766 (1993). More specifically, fluorescein is used as the first fluorescent indicator and tetramethylrhodamine is used as the second fluorescent indicator such that the tetramethylrhodamine moiety substantially quenches any fluorescent emissions by the fluorescein moiety. Thus, when both dyes are attached to the same oligonucleotide, only the tetramethylrhodamine is capable of generating a fluorescent signal. When the oligonucleotide is cleaved, e.g. via the 5'→3' exonuclease activity of a DNA polymerase, separating the two dyes, the fluorescein becomes capable of generating a fluorescent signal. Preferably, in this embodiment, the excitation beam is generated from the 488 nm emission line of an argon ion laser. In accordance with the invention, in a PCR the production of "free" fluorescein in this embodiment is proportional to the amount of DNA synthesis catalyzed by the DNA polymerase employed, and hence, the amount of amplification product. In this embodiment, preferably the first fluorescent indicator is fluorescein, e.g. 6-FAM (available from Applied Biosystems, Foster City), and the second fluorescent indicator is either tetramethylrhodamine or 2',4',5',7',tetrachloro4,7-dichlorofluorescein.

Such oligonucleotide probes of the invention can be synthesized by a number of approaches, e.g. Ozaki et al, Nucleic Acids Research, 20: 5205–5214 (1992); Agrawal et al, Nucleic Acids Research, 18: 5419–5423 (1990); or the like. Preferably, the oligonucleotide probes are synthesized on an automated solid phase DNA synthesizer using phosphoramidite chemistry, e.g. Applied Biosystems, Inc. model 392 or 394 DNA synthesizer (Foster City, Calif.). The first and second fluorescent indicators can be covalently attached to predetermined nucleotide of an oligonucleotide by using nucleoside phosphoramidite monomers containing reactive groups. For example, such reactive groups can be on a phosphate, or phosphate analog, e.g. Agrawal et al (cited above), on the 5' hydroxyl when attachment is to the 5' terminal nucleotide, e.g. Fung et al, U.S. Pat. No. 4,757,141 or Hobbs Jr., U.S. Pat. No. 4,997,928, and on base moieties, e.g. as disclosed by Ruth, U.S. Pat. No. 4,948,882; Haralambidis et al, Nucleic Acids Research, 15: 4857–4876 (1987); Urdea et al, U.S. Pat. No. 5,093,232; Cruickshank U.S. Pat. No. 5,091,519; Hobbs Jr. et al, U.S. Pat. No. 5,151,507; or the like. Most preferably, nucleotides having pyrimidine moieties are derivatized. In further preference, the 3' terminal nucleotide of the oligonucleotide probe is blocked or rendered incapable of extension by a nucleic acid polymerase. Such blocking is conveniently carried out by the attachment of a phosphate group, e.g. via reagents described by Horn and Urdea, Tetrahedron Lett., 27: 4705 (1986), and commercially available as 5' Phosphate-ONIM from Clontech Laboratories (Palo Alto, Calif.). Preferably, the oligonucleotide probe is in the range of 1560 nucleotides in length. More preferably, the oligonucleotide probe is in the range of 18–30 nucleotides in length.

The separation of the first and second fluorescent indicators within the oligonucleotide probe can vary depending on the nature of the first fluorescent indicator and second fluorescent indicator, the manner in which they are attached, the illumination source, and the like. Guidance concerning the selection of an appropriate distance for a given embodiment is found in numerous references on resonant energy transfer between fluorescent molecules and quenching molecules (also sometimes referred to as "donor" molecules and "acceptor" molecules, respectively), e.g. Stryer and Haugland, Proc. Natl. Acad. Sci., 58: 719–726 (1967); Clegg, Meth. Enzymol., 211: 353–388 (1992); Cardullo et al, Proc. Natl. Acad. Sci., 85: 8790–8794 (1988); Ozaki et al (cited above); Haugland (cited above); Heller et al, Fed. Proc., 46: 1968 (1987); and the like. The first and second fluorescent indicators must be close enough so that substantially all, e.g. 90%, of the fluorescence from the first fluorescent indicator is quenched. Typically, for energy transfer-based quenching, the distance between the first and second fluorescent indicators should be within the range of 10–100 angstroms. Preferably, the first and second fluorescent indicators are separated by between about 4 to 10 nucleotides, and more preferably, they are separated by between 4 and 6 nucleotides, with the proviso that there are no intervening secondary structures, such as hairpins, or the like. Preferably, either the first or second fluorescent indicator is attached to the 5' terminal nucleotide of the oligonucleotide probe.

Clearly, related embodiments of the above may be employed wherein the first fluorescent indicator is attached to an oligonucleotide probe with another nonfluorescent quenching molecule, instead of a second fluorescent indicator. In such embodiments, the second fluorescent indicator could be virtually any spectrally resolvable fluorescent dye that did not interact with the amplification products.

B. Reaction Chamber

An important feature of the present invention is the provision in the fluorescent detection apparatus of a reaction chamber that is designed to reduce spurious fluorescence from outside sources. As stated above, reproducible and accurate results in the present apparatus depend on low levels of background flourescence. This is particularly important in configurations of the apparatus that include multiple sample wells, as in the embodiment described in FIG. 2. Fluorescing contamination, such as flakes of skin or hairs present in the tube-holders, can add differential increments to the background measured in each reaction chamber. Moreover, as is shown below, such background is not constant over the fluorescence spectrum measured, but rather has a characteristic peak fluorescence emission that varies according to the contamination source. While such differential background can be subtracted by measuring a "blank" spectrum for each tube, it significantly reduces the signal-to-noise ratio.

The need for reduction of background fluorescence is particularly important in the context of an analytical thermal cycler (ATC) apparatus, as described above and in application Ser. No. 08/235,411, abandoned. This apparatus combines thermal cycling with optical real time detection of DNA amplification during PCR in a "plate reader" format, so that multiple tubes are cycled and monitored simultaneously. It has been found that tube-holder contamination such as from spilled sample or skin flakes can add intensity to individual signals.

In experiments carried out in support of the present invention, it has been found that background attributable to contamination within the tube-holder can be significantly reduced by carrying the reaction out in a tube that is textured in the region supported by the tube-holder walls. In the context of the present invention "texturing" implies surface characteristics that impart cloudy or translucent optical transmission properties to the tube, and that can be defined surface roughness and peak density properties.

More specifically, the surface roughness and peak density properties of the tube are such as to significantly reduce background fluorescence detected by the detector in the above apparatus, in response to spurious, background fluorescence emission related to contamination on the tube holder wall portion. As will be seen below, surface roughness, measured by average depth of "valleys" forming the texture, is preferably 0.0002 to 0.003 inch (0.2 to 3 mils) and more preferably, less than 0.001 inch (1 mil). Preferred peak density is 50 to 500 peaks/0.5 inch line, more preferably 200–500 peaks/0.5 inch line. Surface roughness characteristics can be measured by conventional methods. For example, peak density, expressed as peaks/0.5 line inch, and average valley depth, measured in inches, can be measured using a profilometer device, such as a Hommel T-1000 Profilometer (Tubingen, Germany), in which a stylus is run over the surface. In the context of the present invention, such profilometer measurements may be difficult to make, since the preferred tubes are both curved and small. However, it will be appreciated that an estimate of the texture of a tube used in the present invention can be made by forming a flat textured surface from an analogous mold or forming a flat surface texture by an analogous process to that process used to form the tube texture, then measuring the resulting peak and valley profile, as discussed above. This measurement will provide an estimate of the roughness or texturing parameters of the tube.

It is appreciated that such background emission could also be eliminated by employing a completely opaque tube, i.e., not capable of transmitting light, to serve the objective of substantially reducing background emissions; however, for the particular purpose of using the tubes for reaction mixtures, the translucent feature provides the advantage that the presence of sample or reaction mixture in the tube can be visually or electronically monitored. Translucent or textured tubes made in accordance with the present invention significantly reduce background fluorescence in comparison to the background fluorescence measured from a comparable clear tube or from the sample well itself.

Generally, tubes formed in accordance with the present invention will be molded from plastic, such as polypropylene or polycarbonate. These plastics are commonly used in PCR analysis, because they are inert and do not promote non-specific binding of biological samples. However, it is appreciated that any material having the general optical and chemical properties described above will be appropriate for use in forming such tube.

The entire tube may be textured to adapt to a variety of sample holder configurations; however, the textured portion of the tube will be at least that portion that is in contact with the sample portion of the tube. Minimally, the textured portion will include any regions from which external fluorescence can be detected, according to the geometry of the detection means present in the fluorescence monitoring apparatus in which the tube is used.

The textured region of the tube can be formed in one or more of a number of means. Results from experiments carried out in support of the present invention using tubes having textured regions formed by different methods are provided in Tables 1 and 2 below. Each tube was placed in an empty well of an analytical thermal cycler (ATC) having multiple reaction chambers as described above. The data shown in Table 1 are from tubes were placed in a well (well 51) known to be moderately contaminated with fluorescing contamination. A fluorescence spectrum taken of the well indicated that the fluorescence maximum for the contamination was at the bin 12 region of the CCD sampling device of the ATC. This region represents light of a wavelength of about 544 nm. At this region, the empty well fluoresced 1300 A/D units of light (an A/D unit is a relative unit of fluorescent light intensity; any units can be used in such measurements, so long as they form a continuum between appropriate blank (closed shutter darkness) and 100% transmittance values). Test sample tubes were individually placed in the well and light emission recorded. Values obtained are shown in Table 1 as Average Signal Intensity relative to a closed shutter condition in which no excitatory light was transmitted to the tube and as percent Transmitted Light, where 100% is defined by the amount of light emitted by the well in the absence of the tube.

Table 2 shows transmission values from a well (well 50) known to be highly contaminated (2769 A/D units of light in the absence of a tube). Tables 1 and 2 show that standard polypropylene tubes either slightly enhanced transmission of light from contamination sources (Table 1) or slightly reduced it (Table 2), depending on the amount of contamination present.

As shown by the data presented in Tables 1 and 2, various texturing means are effective to produce texturing characteristics that significantly block emissions of light emanating from contaminated sources in the wells. For comparative purposes, a tube made translucent by inclusion of titanium dioxide in the polypropylene during polymerization of the polymer forming the region was also tested. Such tubes were more effective than clear tubes in reducing contamination-source light transmissions (Table 2), but less effective than textured tubes.

TABLE 1

| Tube/Condition | Average Signal Intensity (A/D units @ bin 12) (Values Adjusted so Shutter Shut = 0) | Percent Transmitted Light |
| --- | --- | --- |
| Shutter Shut | 0 | 0% |
| Chemical Etched Texture | 901 | 69% |

TABLE 1-continued

| Tube/Condition | Average Signal Intensity (A/D units @ bin 12) (Values Adjusted so Shutter Shut = 0) | Percent Transmitted Light |
|---|---|---|
| EDM Etched Texture | 1038 | 80% |
| Sandpaper Roughened | 1143 | 88% |
| Titanium Dioxide Filled | 1322 | 102% |
| Clear Tubes | 1482 | 114% |
| Empty Well | 1300 | 100% |

TABLE 2

| Tube/Condition | Average Signal Intetensity (A/D units @ bin 12) (Values Adjusted so Shutter Shut = 0) | Percent Transmitted Light |
|---|---|---|
| Shutter Shut | 0 | 0% |
| Chemical Etched Tex- | 1393 | 50% |
| EDM Etched Texture | 1584 | 57% |
| Sandpaper Roughened | 1603 | 58% |
| Titanium Dioxied Filled | 1855 | 67% |
| Clear Tubes | 2272 | 82% |
| Empty Well | 2769 | 100% |

Without committing to an underlying mechanistic theory for the invention, it is noted that such texturing scatters light impinging upon the surface of the tube, and prevents or reduces the amount of light that is directed to the tube interior from outside sources within the tube-holder.

There are a number of ways of creating texture on the surface of the tube to effect the desired reduction in background fluorescence. In one general embodiment, a molded tube may be cast in a textured mold, which then imparts to the tube a textured, irregular surface. Means for making a textured mold are well known in the art, but generally involve etching the mold, by chemical or physical means, such as discussed below.

Representative etching means include bead blasting of the mold cavity, electron discharge machining of the mold cavity and chemical etching of the mold cavity. It should be noted that all these means are preferably carried out on the mold surface in such a way as to produce texturing on the exterior surface of the tube. Although texturing of the interior surface of the tube will also reduce transmission of light from external fluorescent sources, such interior texturing is less desirable in the context of the present invention, since it may interfere with the reaction or with the ability to quantitatively remove the reaction mixture from the tube.

Etched metal molds suitable for forming textured tubes are made in a number of ways. One conventional means for creating such a mold is to "bead blast" the cavity of the mold. This process removes small pockets of metal from the mold surface by hitting the surface with high velocity particles, such as particles of sodium bicarbonate (baking soda).

An etched mold surface can also be formed by an electron discharge machining (EDM) procedure that removes small pockets of metal from the mold by bombarding it with arcs of electricity. As shown in Tables 1 and 2, using such a procedure, light emitted from the contamination in the well was reduced by 20% in the moderately contaminated well and by 43% in the highly contaminated well.

The mold may also be etched by chemical etching means. Generally, according to methods well known in the molding arts, a mask is placed on the mold surface in the area of texture. The mold is then dipped into an acid bath which removes metal from the unmasked areas. This process may be used to produce a highly dense irregular surface pattern on the mold surface. This is a particularly effective and controlled means of producing an outer tube texture, in accordance with the present invention.

Mold Tech (Roehlen Industries, Walnut, Calif.) produces by chemical etching a texture having a specified average thickness as well as defined peaks and valleys. Such textures are well known in the art and are best characterized by their Mold Tech Pattern specification numbers, which are considered industry standards. Table 3 lists a number of exemplary Mold Tech patterns that have been used to form texturing on tubes in accordance with the present invention. The MT-1 1000 (MT-11003 to MT-11005) series texturing patterns is created by blasting a metal mold with a defined size of grit, such as aluminum oxide. The MT-1055 series is created by acid etching.

TABLE 3

| Mold Tech Pattern Specification | Average Depth of Etch |
|---|---|
| MT-11003 | .000195 inch |
| MT-11004 | .000267 inch |
| MT-11005 | .000477 inch |
| MT-11006 | .001002 inch |
| MT-11007 | .001468 inch |
| MT-1055-2 | .000063 inch |
| MT-1055-3 | .000072 inch |
| MT-1055-4 | .000093 inch |
| MT-1055-5 | .000097 inch |
| MT-1055 | .000145 inch |

As shown from the data presented in Tables 1 and 2, tubes from chemically etched molds (MT-1055-5) produced significant reductions in contamination emissions from moderately (31% reduction) and highly (50% reduction) contaminated wells. As discussed above, while it is difficult to precisely measure texturing characteristics of these patterns in the context of the small tubes prepared for use in the embodiment illustrated, a good estimate of their parameters can be made by preparing analogous flat surfaces using the same mold treatment method, and measuring the average peak density and average valley depth of such surfaces. The MT-1055-5 texture has a peak density of 88 peaks/0.5 inch line and an average thickness (depth of etch) of 0.00097 inch. Other particularly efficacious tubes have been formed from MT-11005, having a peak density of 379 peaks/0.5 inch line and an average thickness of 0.000477 inch, and MT-11006, having a peak density of 283 peaks/0.5 inch line and an average thickness of 0.001002 inch. More generally, it is appreciated that a texture having a peak density of between about 50 and 500 peaks/0.5 inch line and an average thickness of between about 0.0002 and 0.003 inch will be preferred for use in the invention. More particularly, preferred molding patterns for use in PCR reactions have peak densities at the higher end of the range (200–500 peaks/0.5 inch line) and have thicknesses between 0.0004 and 0.001 inch to maximize both depth and heat transfer.

In another general embodiment, the texturing is produced by abrading or roughening the surface, e.g., with abrasive tape or cloth or by rotating brush abrading in the presence of abrasive particles. In experiments carried out in support of the present invention, it was determined that applying sandpaper (240, 320 or 400 grit) to the outer surface of polypropylene tubes produced tubes capable of blocking at least 12% and 42% of contamination related emissions in the moderately and highly contaminated wells, respectively (Tables 1 and 2).

Figure 3A:
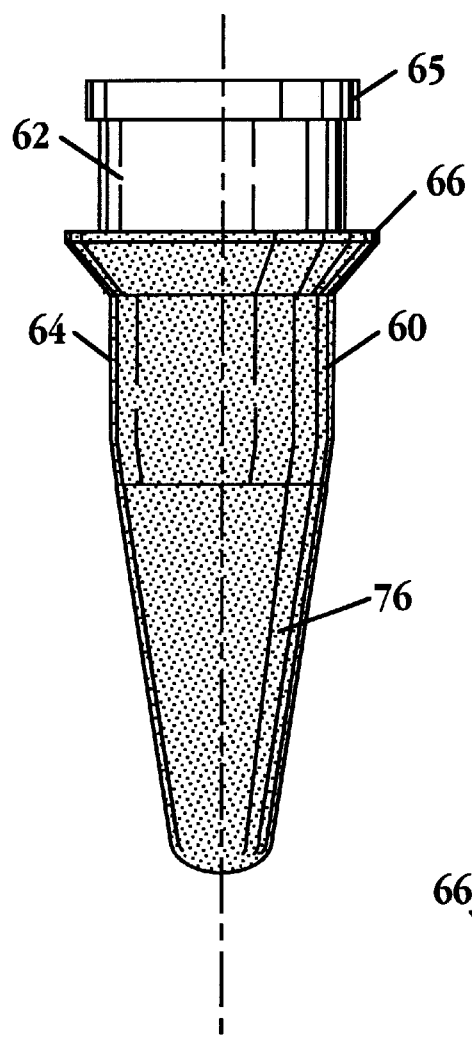
FIG. 3A shows a side view of an optical tube in accordance with the invention.
Figure 3B:
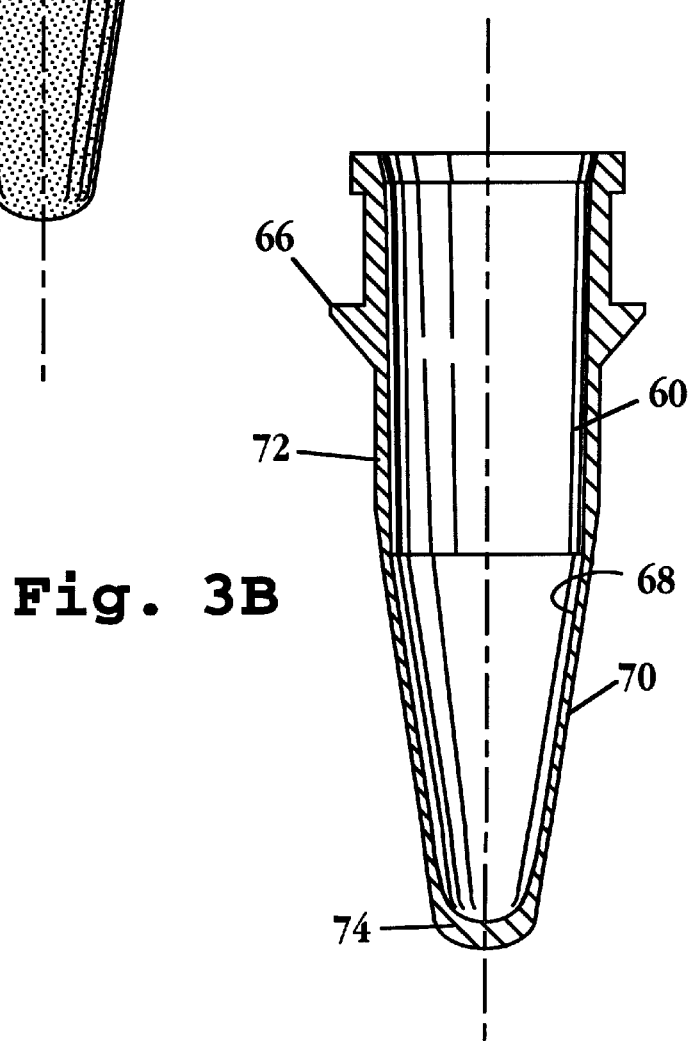
FIG. 3B shows a cross-sectional view of the tube illustrated in FIG. 3A.

FIGS. 3A and 3B show plan and cross-sectional views, respectively, of a tube 60 formed in accordance with the present invention. The tube illustrated has a total volume of about 200 microliters and is formed of virgin polypropylene having no allowable regrind. The tube may also be formed of a comparable grade of polycarbonate.

As illustrated in FIG. 3A, tube 60 has an upper region 62 and a lower region 64 divided by ridge 66. Ridge 66 is constructed and positioned to allow for placement of the tube in a tube holder, as described above. Upper region 62 is bounded at the top of the tube by lip 65, which circumscribes an upper opening in the tube and which may be imprinted with vendor markings. Lip 65 may be constructed to receive a clear cap, as illustrated in FIG. 1, or the opening may be left open, as illustrated here, to permit transmission of an excitation beam to the sample.

With reference to FIG. 3B, the ridge and other surface relief features visible on the outer surface of tube 60 are not reflected in inner surface 68, which is preferably left smooth to facilitate quantitative sample transfer from the tube. In the embodiment illustrated, it can be seen that the wall thickness of the tube varies between the various regions of the tube. In the 200 µl tube 60 illustrated, the wall thickness varies from 0.009 inch in the lower region indicated at 70 to 0.015 inch in the upper portion of tube indicated at 72. The base of the tube 74 is thicker (0.029 inch) to withstand higher pressures, such as are encountered during centrifugation.

Returning to FIG. 3A, lower region 64 is shown as a textured surface 76 applied according to Mold Tech pattern MT1055-5 having an average etch depth of 0.00097 inch, as described above.

Figure 4:
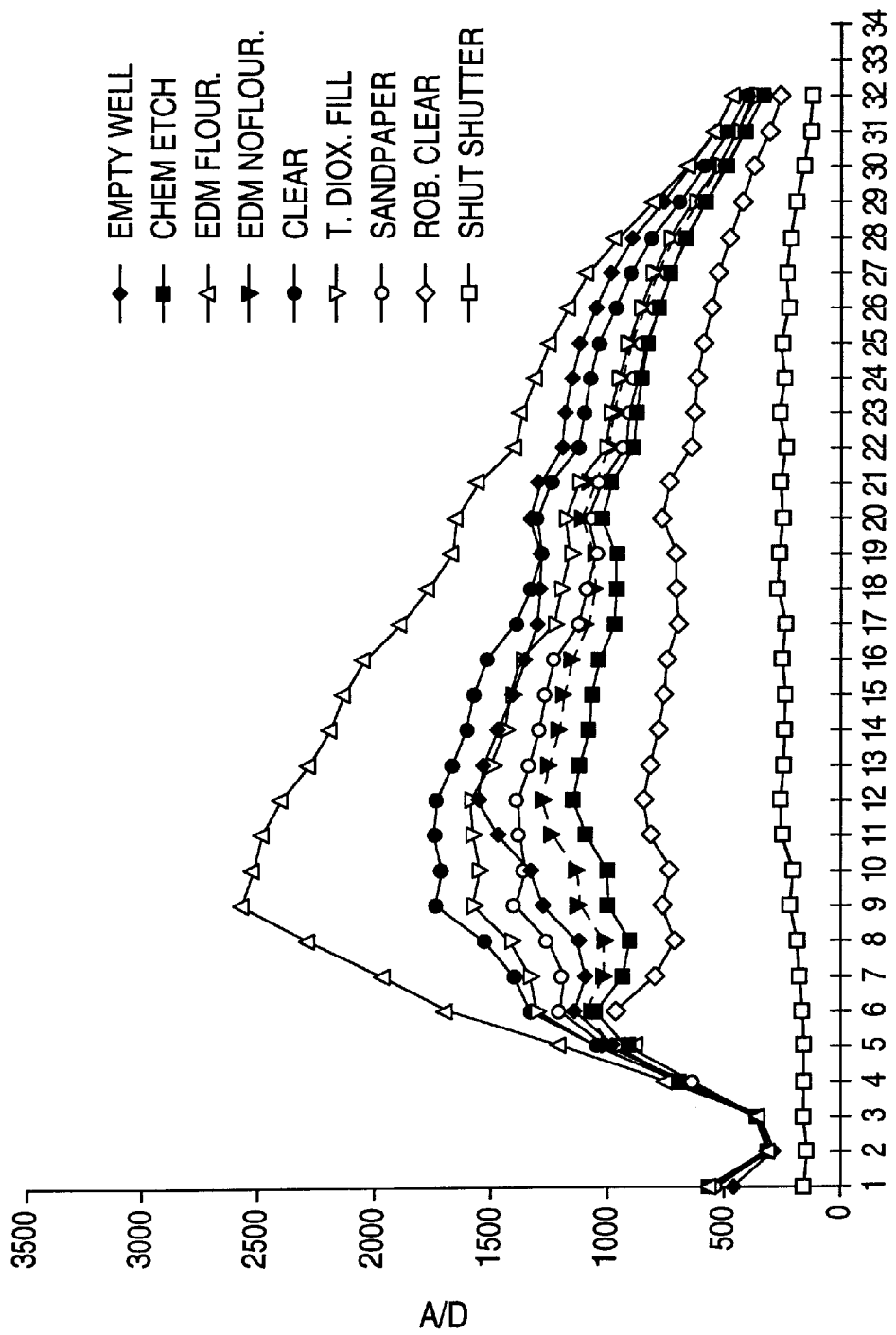
FIG. 4 shows an emission spectra measured from a moderately contaminated well in a ATC apparatus fitted with various tubes.
Figure 5:
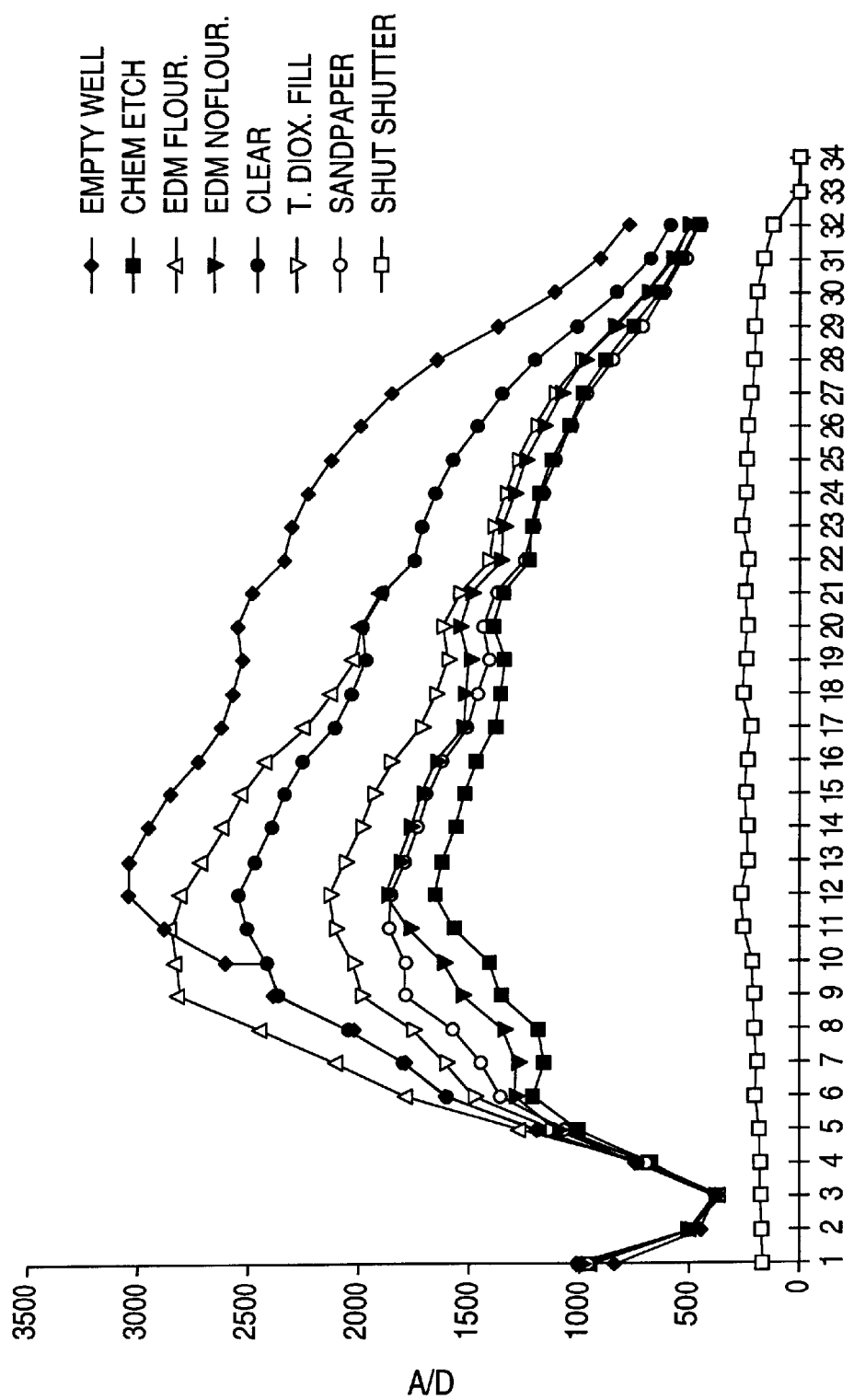
FIG. 5 shows an emission spectrum measured from a highly contaminated well in a ATC apparatus fitted with various tubes.

Polypropylene tubes constructed according to the specifications of the tube illustrated in FIG. 3A and having textured or translucent lower regions were tested in placed in a highly contaminated well of an ATC, as described above. Full emission spectra were recorded for each tube after excitation at 488 nm using a CCD detection system, where bins 1–32 correspond approximately to 500–600 nm emission wavelengths. FIGS. 4 and 5 shows a comparison of spectra recorded from a moderately contaminated well (well 51) and a highly contaminated well (well 50) of an ATC as follows: empty well (diamonds), a tube textured by EDM and displaying high initial fluorescence under a black light (solid triangles), a clear MicroAmp™ tube (closed circles), a translucent tube containing titanium dioxide (crosses), a tube roughened by sandpaper treatment (open circles), a tube textured by EDM and displaying low initial fluorescence under a black light (crosses), and a tube having chemically etched on its lower surface Mold Tech pattern MT1055-5 (solid squares). The closed shutter readings at are shown as stippled squares in both figures.

The following examples illustrate, but in no way are intended to limit the present invention.

EXAMPLE 1

Real time monitoring of PCR amplification of DNA encoding Q-actin from various starting concentrations of target DNA A 296 basepair segment of a target DNA encoding human B-actin was amplified by PCR from various starting amounts in the range of 5×103 to 1×106 copies of target DNA. The following primers and probe were employed:

5'-TCACCCACACTGTGCCCATCTACGA SEQ ID NO: 01

(forward primer)

5'-CAGCGGAACCGCTCATTGCCAATGGT SEQ ID NO: 02

(reverse primer)

5'-(FAM)-TGCCCT(TMR) CCCCCATGCCATCCTGCGT SEQ ID NO: 03

(probe)

wherein "FAM" indicates a fluorescein molecule coupled to the oligonucleotide by reacting an NHS-ester group attached to the fluorescein's 6 carbon with a 5'aminophosphate attached to the 5'terminal deoxyadenosine of the oligonucleotide in accordance with Fung et al, U.S. Pat. No. 5,212,304; and wherein a tetramethylrhodamine molecule is coupled to the base moiety of the adjacent thymidine at nucleotide position 7 via the amino linking agent disclosed by Urdea et al, U.S. Pat. No. 5,093,232.

PCRs were carried out in 0.2 mL MicroAmp tubes (Perkin-Elmer, Norwalk, Conn.) with the following components: 10 mM Tris-HCI, pH 8.3, 50 mM KCL 3.5 mM MgCl2, 200 µM each of the nucleoside triphosphates (with dUTP substituted for dTTP in accordance with U.S. Pat. No. 5,035,996 to prevent carryover contamination), 300 nM each of forward and reverse primers, AmpliTaq (Perkin-Elmer, Norwalk, Conn.) at 0.05 U/µL. To this mixture was added 5 µL Raji DNA (Applied Biosystems, Foster City, Calif.) at 10 ng/µL, 5 µL probe at 2 µM, and 1 µL uracil N-glycosylase at 1 unit/µL to bring the reaction volume to 51 µL. Heating and cooling cycles were carried out in a model 9600 Thermal Cycler (Perkin-Elmer, Norwalk, Conn.) fitted with a sample holder cover containing the sample interface components of the invention. The following temperature profile was employed: hold for 2 minutes at 50° C.; hold for 10 minutes at 95° C.; cycle through the following temperatures 40 times: 92° C. for 15 seconds, 54° C. for 15 seconds, 72° C. for 1 minute; then hold at 72° C.

Figure 6:
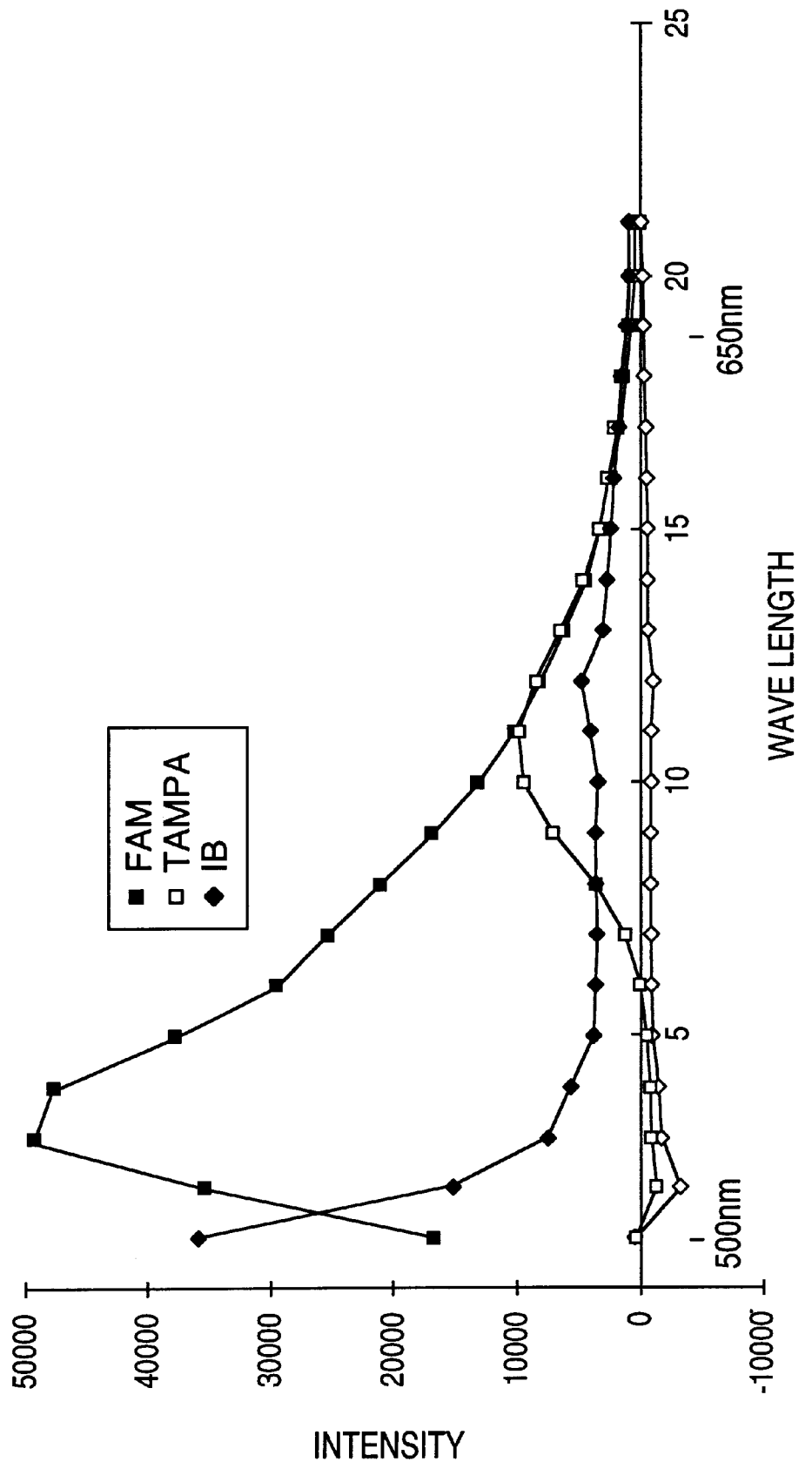
FIG. 6 shows spectrally separated fluorescent intensity data for a tetramethylrhodamine fluorescent indicator, a fluorescein fluorescent indicator, and instrument background registered by a CCD array of the preferred embodiment described below.

FIG. 6 illustrates data showing the emission spectra of the fluorescein and tetramethylrhodamine dyes employed as indicators above and fluorescence due to extraneous sources in the apparatus.

Figure 7:
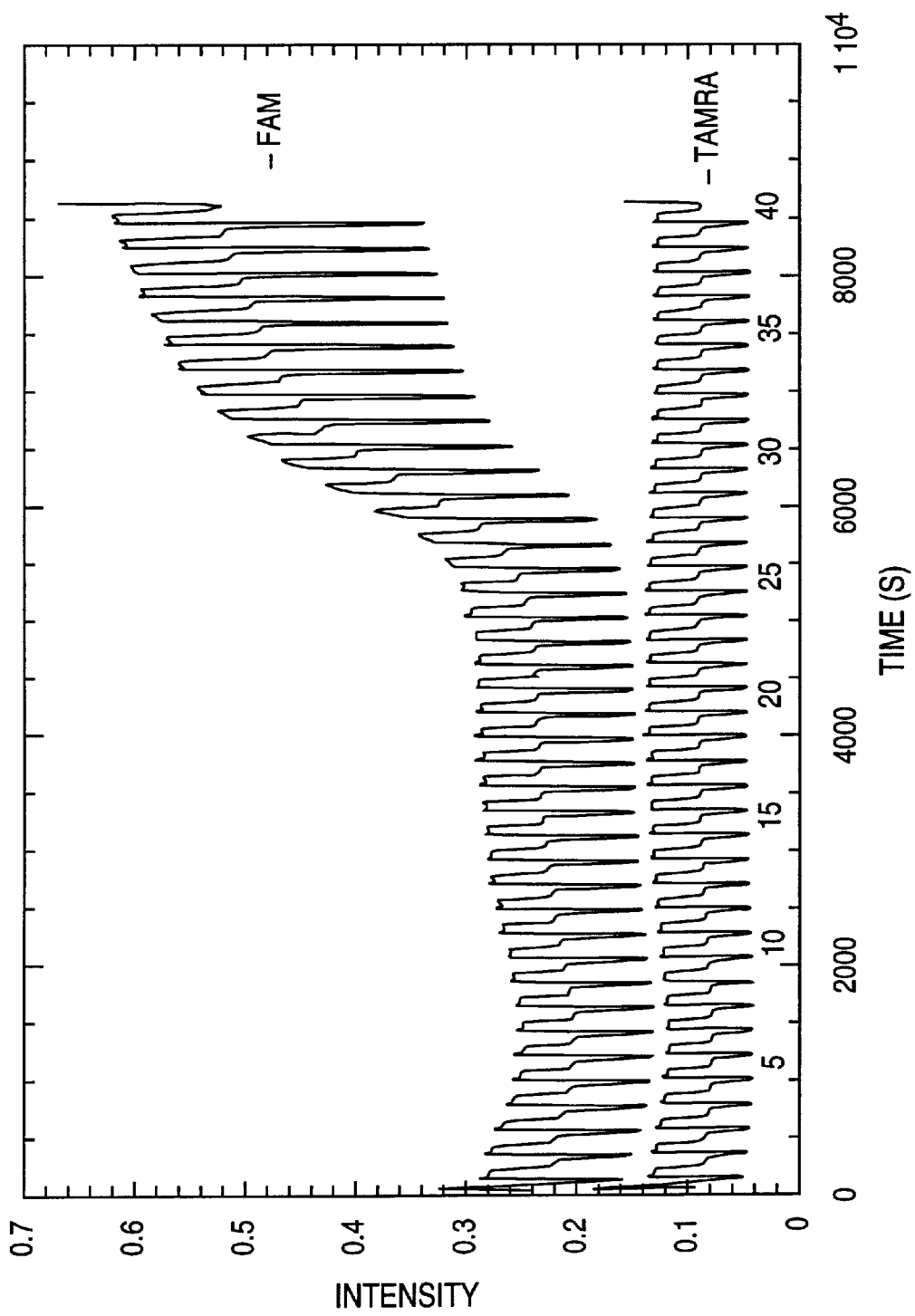
FIG. 7 shows the time dependence of fluorescent signals from a fluorescein dye proportional to the amplification product (first fluorescent indicator) and a tetramethylrhodamine dye employed as a second fluorescent indicator during a typical PCR.
Figure 8:
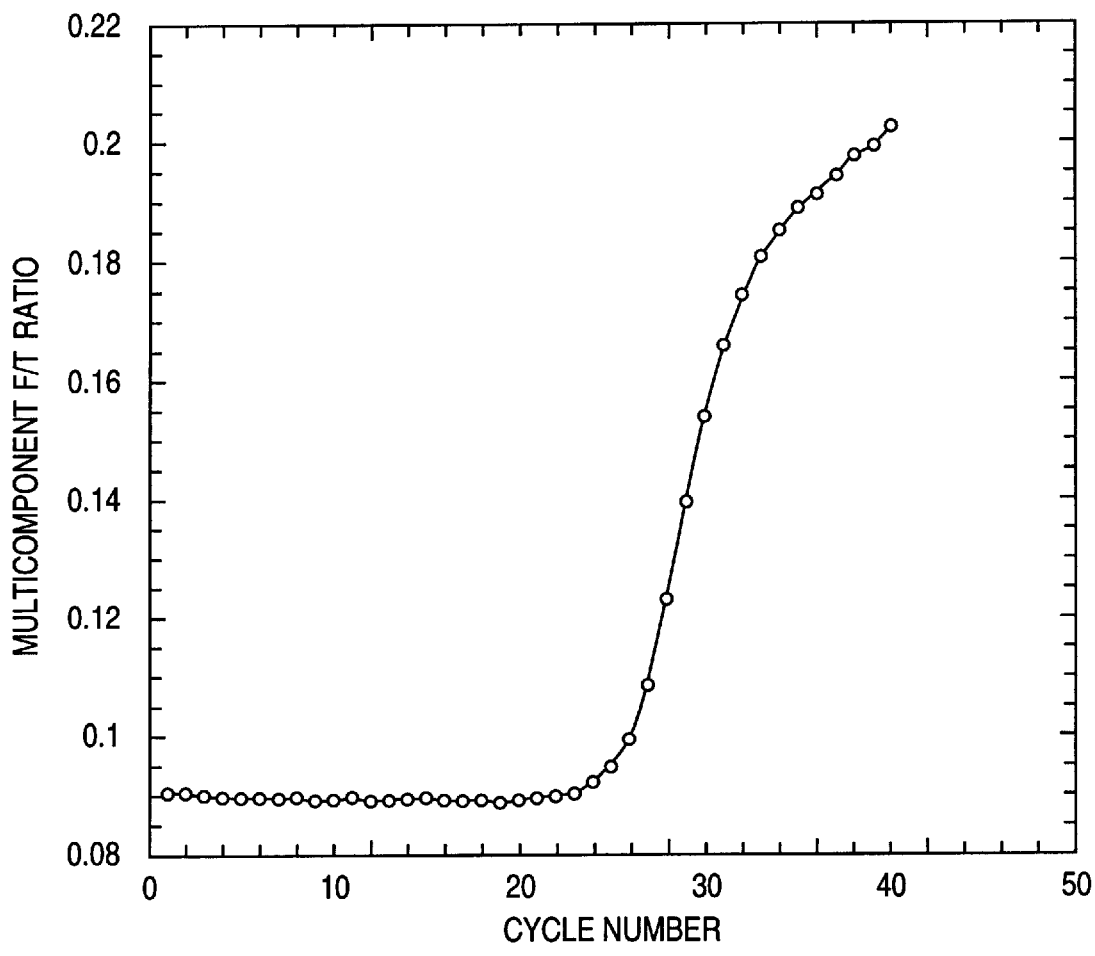
FIG. 8 shows the cycle dependence of the ratio of the intensities of the fluorescein and tetratmethylrhodamine dyes from the same PCR whose time dependent data is shown in FIG. 6.

FIG. 7 illustrates data showing fluorescein fluorescent intensity and tetramethylrhodamine fluorescent intensity as a function of cycle number. The high frequency oscillations in intensity reflect the temperature dependence of the fluorescent emission of the two dyes. An increase in base line fluorescence for both dyes between cycles 10 and 28 is a system—based variation. In FIG. 8, which illustrates the ratio of fluorescein-to-tetramethylrhodamine fluorescent intensity from the same data, the system-based variation is eliminated and the RMS of fluctuations in the readout signal, that is, the ratio of fluorescent intensities, is less than 1% of the average magnitude of the measured ratio.

Figure 9:
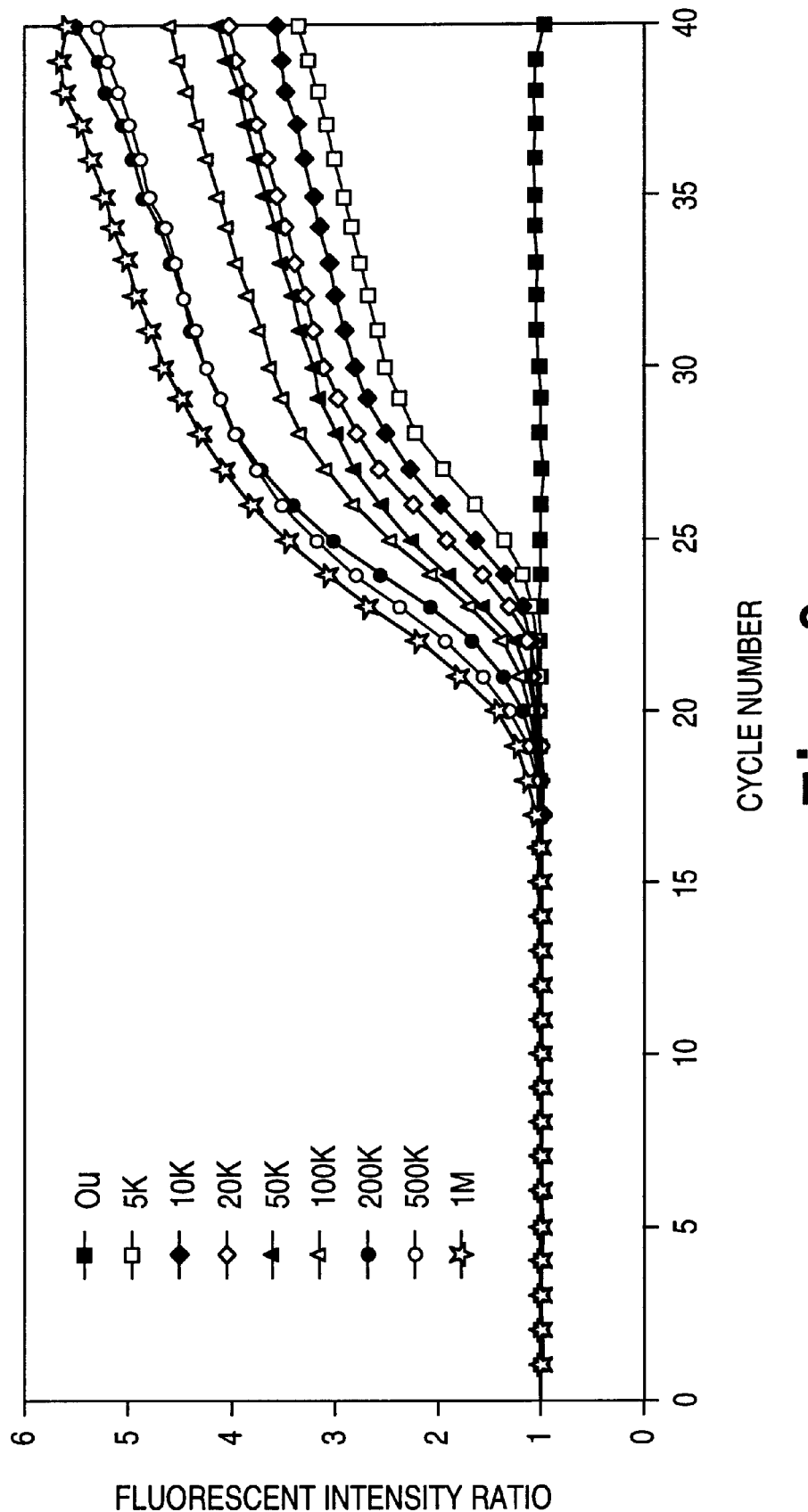
FIG. 9 shows data relating the amount of amplification product to cycle number in separate PCRs having different starting concentrations of the same target nucleic acid.

FIG. 9 illustrates data from PCR of the Martin DNA starting from amounts ranging from 5000 target molecules to $10^6$ target molecules as indicated in the figure.

While the invention has been described with reference to specific methods and embodiments, it will be appreciated that various modifications and changes may be made without departing from the invention.

It is claimed:

1. Fluorescence monitoring apparatus for measuring fluorescent emission from a sample in response to sample irradiation by an emission beam, comprising an excitation beam source, transmission means capable of directing an excitation beam from said excitation beam source into the sample and further capable of carrying fluorescent signals from said sample to a detection means, a tube-holder having a wall portion capable of supporting a tube, a tube for holding the sample, said tube having (i) a clear end region for transmitting said excitation beam into said sample and for transmitting fluorescent signals from said sample to said transmission means, and (ii) an opposite closed end region, and detection means capable of detecting fluorescent emissions from the sample in the tube, wherein said tube is textured in the region of the tube supported by said tube-holder wall portion and in said opposite closed end region, and the textured region is characterized by a surface roughness and peak density effective to significantly reduce background fluorescence detected by said detection means in response to fluorescence emission related to contamination on the tube holder wall portion.

2. The apparatus of claim 1, wherein said tube is formed of a polymer material selected from the group consisting of polypropylene and polycarbonate.

3. The apparatus of claim 1, wherein textured region of said tube has a textured outer surface characterized by a peak density of between about 50 and 500 peaks/0.5 inch line.

4. The apparatus of claim 3, wherein said peak density is between about 200 and 500 peaks/0.5 inch line.

5. The apparatus of claim 3, wherein the surface roughness is characterized by an average depth of between 0.0002 and 0.003 inch.

6. The apparatus of claim 5, wherein the surface roughness is characterized by an average depth of less than 0.001 inch.

7. A method for reducing fluorescence background in a fluorescence monitoring apparatus designed for detecting fluorescent emission from a sample contained in a sample tube, said method comprising providing a sample tube having (i) a clear end region for transmitting excitation beams into said tube and for transmitting fluorescent signals from a sample contained in said tube, and (ii) an opposite closed end region capable of being received and supported by wall portions of a tube-holder in said apparatus, wherein the surface of the tube supported by the wall portion has a surface roughness and peak density effective to significantly reduce background fluorescence detected by said apparatus in response to fluorescence emission related to contamination on the tube holder wall portion, placing said tube into a tube-holder of the apparatus, and measuring fluorescence emission emitted from a sample in said tube, wherein background fluorescence related to contamination on the tube holder wall portion is significantly reduced.

8. The method of claim 7, wherein said surface has a surface peak density of between about 50 and 500 peaks/0.5 inch line.

9. The method of claim 8, wherein said peak density is between about 200 and 500 peaks/0.5 inch line.

10. This method of claim 8, wherein the surface roughness is characterized by an average depth of between 0.0002 and 0.003 inch.

11. The method of claim 10, wherein the surface roughness is characterized by an average depth of less than 0.001 inch.

12. The method of claim 7, wherein said surface has been formed by casting the tube in a mold having an etched mold surface.

13. The method of claim 7, wherein said surface has been formed by abrasion.

14. The apparatus of claim 1, wherein said transmission means includes a lens positioned between said excitation beam source and said tube, wherein said lens is capable of focusing said excitation beam into the sample in said tube, and said lens is further capable of collecting said fluorescent signals from said sample.

15. The apparatus of claim 1, wherein the tube-holder is capable of supporting a plurality of tubes.

16. The method of claim 7, wherein said method comprises detecting fluorescent emission from a plurality of samples contained in a plurality of tubes.

* * * * *

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 25 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

TCACCCACAC TGTGCCCATC TACGA                              25

(2) INFORMATION FOR SEQ ID NO:2:

(i) SEQUENCE CHARACTERISTICS:
      (A) LENGTH: 26 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:2:

CAGCGGAACC GCTCATTGCC AATGGT                             26

(2) INFORMATION FOR SEQ ID NO:3:

(i) SEQUENCE CHARACTERISTICS:
      (A) LENGTH: 26 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:3:

ATGCCCTCCC CCATGCCATC CTGCGT                             26